(12) United States Patent
Pohl et al.

(10) Patent No.: US 9,592,458 B2
(45) Date of Patent: Mar. 14, 2017

(54) ION EXCHANGE FOAMS TO REMOVE IONS FROM SAMPLES

(71) Applicant: DIONEX CORPORATION, Sunnyvale, CA (US)

(72) Inventors: Christopher A. Pohl, Union City, CA (US); Rosanne W. Slingsby, Pleasanton, CA (US); Jing Hong, Cupertino, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 323 days.

(21) Appl. No.: 14/140,690

(22) Filed: Dec. 26, 2013

(65) Prior Publication Data

US 2015/0182875 A1 Jul. 2, 2015

(51) Int. Cl.
| | |
|---|---|
| *B01D 15/36* | (2006.01) |
| *B01J 39/20* | (2006.01) |
| *B01J 47/00* | (2006.01) |
| *G01N 30/96* | (2006.01) |
| *C08J 5/20* | (2006.01) |

(Continued)

(52) U.S. Cl.
CPC ............ *B01D 15/361* (2013.01); *B01J 39/20* (2013.01); *B01J 47/007* (2013.01); *B01L 3/502* (2013.01); *B01L 3/5635* (2013.01); *C08J 5/20* (2013.01); *G01N 30/20* (2013.01); *G01N 30/24* (2013.01); *G01N 30/96* (2013.01); *G01N 35/10* (2013.01); *B01L 2200/026* (2013.01); *B01L 2300/042* (2013.01); *B01L 2300/049* (2013.01); *B01L 2300/0681* (2013.01); *B01L 2300/0832* (2013.01); *B01L 2300/123* (2013.01); *B01L 2400/0478* (2013.01); *C08J 2325/06* (2013.01);

(Continued)

(58) Field of Classification Search
CPC ....... B01D 15/361; B01J 39/20; B01J 47/007; B01L 3/502; B01L 3/5635; G01N 30/96; G01N 30/20; G01N 35/10; C08J 5/20
USPC .......................................................... 521/25
See application file for complete search history.

(56) References Cited

U.S. PATENT DOCUMENTS

| | | |
|---|---|---|
| 3,024,207 A | 3/1962 | Shaw et al. |
| 3,481,477 A | 12/1969 | Farr |

(Continued)

FOREIGN PATENT DOCUMENTS

| | | |
|---|---|---|
| CN | 1313790 A | 9/2001 |
| EP | 0385587 B1 | 12/1993 |

(Continued)

OTHER PUBLICATIONS

Braun et al., "Ion-Exchange Foam Chromatography—Part I. Preparation of Rigid and Flexible Ion-Exchange Foams," Anal. Chimica Acta., 64, 45-54, 1973.

(Continued)

*Primary Examiner* — Michael M Bernshteyn
(74) *Attorney, Agent, or Firm* — Timothy J. Ohara

(57) ABSTRACT

A method of making an ion exchange foam is described. The method includes forming an aqueous phase by suspending an ion exchange resin in an aqueous solvent. An organic phase is formed by mixing at least a divinylbenzene, a monomer, and a surfactant. The formed aqueous phase is mixed with the formed organic phase to form an emulsion. The emulsion is polymerized to form the ion exchange foam.

(Continued)

The ion exchange foam can be used with a plurality of sample vials in an autosampler.

20 Claims, 5 Drawing Sheets

(51) Int. Cl.
*G01N 30/20* (2006.01)
*B01L 3/00* (2006.01)
*G01N 30/24* (2006.01)
*G01N 35/10* (2006.01)
*G01N 35/04* (2006.01)

(52) U.S. Cl.
CPC ....... *C08J 2425/06* (2013.01); *G01N 35/1095* (2013.01); *G01N 2035/0441* (2013.01)

(56) References Cited

U.S. PATENT DOCUMENTS

| | | | |
|---|---|---|---|
| 4,263,407 A | 4/1981 | Reed, Jr. | |
| 4,644,807 A | 2/1987 | Mar | |
| 5,037,859 A | 8/1991 | Williams, Jr. et al. | |
| 5,567,309 A | 10/1996 | Classon et al. | |
| 5,583,162 A | 12/1996 | Li et al. | |
| 5,653,922 A | 8/1997 | Li et al. | |
| 5,760,097 A | 6/1998 | Li et al. | |
| 5,864,957 A | 2/1999 | Small | |
| 6,100,306 A | 8/2000 | Li et al. | |
| 6,290,853 B1 | 9/2001 | Allmer et al. | |
| 6,365,683 B2 | 4/2002 | Podszun et al. | |
| 6,710,093 B2 | 3/2004 | Yao et al. | |
| 6,750,261 B1 | 6/2004 | Clear et al. | |
| 2002/0132106 A1 | 9/2002 | Dyer et al. | |
| 2002/0198271 A1 | 12/2002 | Thunhorst et al. | |
| 2003/0062311 A1 | 4/2003 | Yao et al. | |
| 2004/0122117 A1 | 6/2004 | Yamanaka et al. | |
| 2005/0139549 A1 | 6/2005 | Yoshida et al. | |
| 2007/0282025 A1 | 12/2007 | Collier et al. | |
| 2010/0224012 A1 | 9/2010 | Modic et al. | |
| 2010/0326847 A1 | 12/2010 | Jonschker et al. | |
| 2011/0259818 A1 | 10/2011 | Tamada et al. | |

FOREIGN PATENT DOCUMENTS

| | | | | |
|---|---|---|---|---|
| EP | 0763064 B1 | 8/2001 | | |
| GB | 874576 | 8/1961 | | |
| GB | 874576 A | * 8/1961 | ............. B01J 39/20 | |
| JP | 3015870 B2 | 3/2000 | | |
| JP | 2009062512 A | * 3/2009 | | |
| WO | 9533553 A1 | 12/1995 | | |
| WO | 9719347 A1 | 5/1997 | | |
| WO | WO2004007081 A1 | 1/2004 | | |
| WO | 2010102061 A1 | 9/2010 | | |
| WO | 2010129077 A1 | 11/2010 | | |
| WO | 2004005355 A1 | 1/2014 | | |

OTHER PUBLICATIONS

Thermo Scientific Dionex AS-DV Autosampler Operator's Manual, Document No. 065259, Revision 04, 130 pages, Dec. 2011.
Thermo Scientific Dionex OnGuard II Cartridges-Product Manual, P/N: 031688-07, 34 pages, May 2013.
Dionex Product Manual ASRS(R) 300 CSRS(R) 300, Document No. 031956, Rev. 05, Aug. 2007, 51 pages.
Dionex Product Manual for IonPac(R) AG11 IonPac(R) AS11, Doc No. 034791, Rev. 12, Apr. 7, 2009, 46 pages.
Dionex Product Manual for IonPac(R) CG12A IonPac(R) CS12A, Doc No. 031132, Rev. 09, May 2010, 78 pages.

* cited by examiner

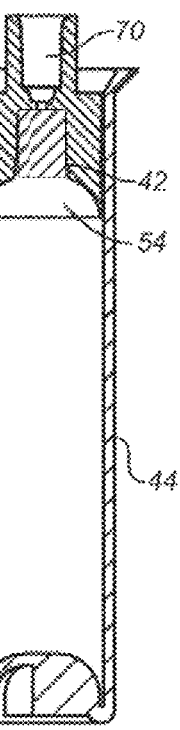
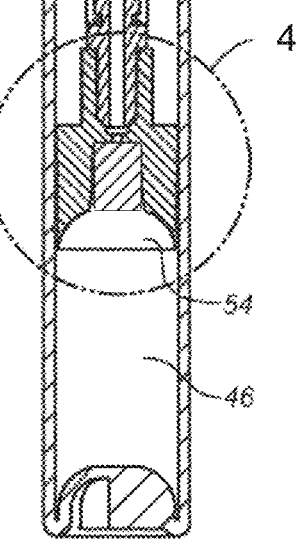
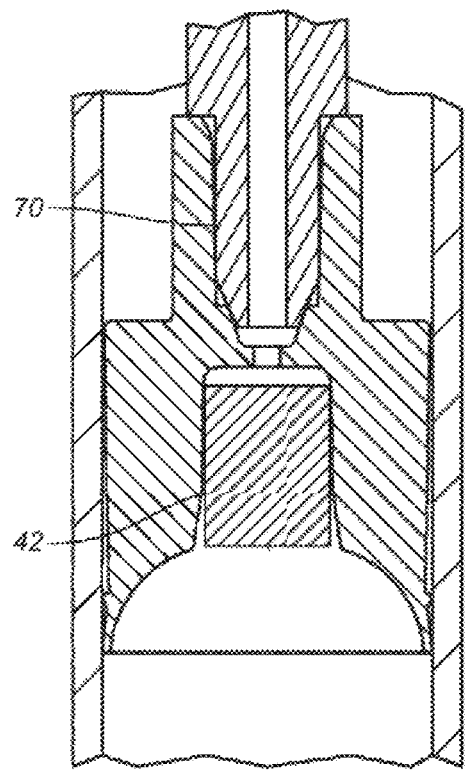
FIG. 2    FIG. 3    FIG. 4

ION EXCHANGE FOAMS TO REMOVE IONS FROM SAMPLES

BACKGROUND

Chromatography is a widely used analytical technique for the chemical analysis and separation of molecules. Chromatography involves the separation of one or more analyte species from other matrix component present in a sample. A stationary phase of a chromatography column is typically selected so that there is an interaction with the analyte. Such interactions can be ionic, hydrophilic, hydrophobic, or combinations thereof. For example, the stationary phase can be derivatized with ionic moieties that ideally will bind to an ionic analytes and matrix components with varying levels of affinity. A mobile phase is percolated through the stationary phase and competes with the analyte and matrix components for binding to the ionic moieties. The mobile phase is a term used to describe a liquid solvent or buffer solution that is pumped into a chromatography column inlet. During this competition, the analyte and matrix components will elute off of the stationary phase as a function of time and then be subsequently detected at a detector. Examples of some typical detectors are a conductivity detector, a UV-VIS spectrophotometer, and a mass spectrometer. Over the years, chromatography has developed into a powerful analytical tool that is useful for creating a healthier, cleaner, and safer environment where complex sample mixtures can be separated and analyzed for various industries such as water quality, environmental monitoring, food analysis, pharmaceutical, and biotechnology.

Under certain circumstances, a sample can have a relatively high concentration of a matrix component compared to the analyte concentration. This can cause an interference and prevent an accurate analysis of the analyte within the sample. In one instance, an excessively high matrix concentration can saturate the conductivity detector skewing the baseline response of the analyte peak of a chromatogram. In another instance, a matrix component can generate a chromatographic peak that overlaps with the analyte peak, and thus, interfere with the analysis. An example of matrix species can be sodium chloride in the trace analysis of perchlorate. As such, the liquid sample will typically be pre-treated to remove or reduce a high concentration of a matrix ion like chloride.

Solid phase extraction is a type of sample pre-treatment that can be used to remove matrix chemicals from a sample. Some solid phase extraction devices require a significant amount of pressure to pass a liquid sample through the solid phase extraction device, which is not well-suited to automated sample pre-treatment with auto-samplers. Other solid phase extraction devices that do not require a significant amount of pressure cannot bind a significant amount of matrix chemicals because of low capacity. It should also be noted that the binding capacity per unit volume of the extraction device needs to be sufficiently large so as to reduce the proportion of the dead volume of the extraction device where the liquid sample cannot be easily recovered. A relatively low dead volume is useful where there is a limited volume of a sample to pre-treat. Thus, Applicant believes that there is a need for solid phase extraction materials that have a high capacity per unit volume sufficient to pre-treat a single sample, require a relatively low pressure, and have a compact size so that it can be adapted to existing auto-sampling instruments.

SUMMARY

A method of making an ion exchange foam includes forming an aqueous phase by suspending an ion exchange resin in an aqueous solvent. An organic phase is formed by mixing at least a divinylbenzene, a monomer, and a surfactant. The formed aqueous phase is mixed with the formed organic phase to form an emulsion. The emulsion is polymerized to form the ion exchange foam.

In regards to the above method, the ion exchange foam may include one or more of the following. The ion exchange foam may contain about 40% to about 60% ion exchange resin by volume. The ion exchange foam may have an exterior shape that is approximately cylindrical or approximately conical. The surfactant may include an oil soluble surfactant, and more specifically a non-ionic oil soluble surfactant. The surfactant may include a sorbitan monooleate. The surfactant may be in a form of a block co-polymer.

In regards to the above method, the polymerizing can include heating the emulsion to a temperature sufficient to initiate an initiator. In one embodiment, the heating can be about 60° C. In one alternative embodiment, the polymerizing can include illuminating the emulsion with an intensity sufficient to initiate an initiator. In another alternative embodiment, the polymerizing can include irradiating the emulsion with an ionizing radiation source at an intensity sufficient to initiate a polymerization. In another embodiment, the initiator is dissolved in the aqueous phase and may include a persulfate. In another embodiment, the initiator may include a cationic water soluble initiator where the ion exchange resin includes an anion exchange resin. The monomer may be a styrenic monomer, an acrylate, a methacrylate, and a combination thereof.

In regards to the above method, the ion exchange resin includes a salt form of a cation exchange resin. The ion exchange resin may be one of a strong cation exchange resin, a weak cation exchange resin, a strong anion exchange resin, a weak anion exchange resin, and a combination thereof.

In regards to the above method, the formed organic phase can be mixed at about 400 rotations per minute and the formed aqueous phase is added to the formed organic phase to form the emulsion.

An ion exchange foam includes a copolymer and an ion exchange resin. The copolymer includes at least a divinylbenzene (DVB) and a monomer where the resulting copolymer has a void volume. The ion exchange resin is disposed in the void volume and is bound to the ion exchange foam. The ion exchange foam includes about 40% to about 60% ion exchange resin by volume.

In regards to the above ion exchange foam, it may include one or more of the following. The ion exchange resin can have a diameter ranging from about 4 microns to about 20 microns. The ion exchange foam can have an ion capacity per unit volume ranging from about 1 milliequivalents per cubic centimeter to about 50 milliequivalents per cubic centimeter. The ion exchange foam can have a flow rate ranging from about 0.5 mL per minute to about 10 mL per minute at a pressure of about 50 pounds per square inch or less where the ion exchange foam is in the form of a cylinder with a diameter of about 5 millimeters and a length of 10 about millimeters. The ion exchange foam can have a permeability ranging from about $1 \times 10^{-11}$ $m^2$ to about $1 \times 10^{-16}$ $m^2$. The monomer may be a styrenic monomer, acrylate, methacrylate, and a combination thereof A method of removing ions from a liquid sample is described. The method includes pushing a plunger cap towards a bottom wall of a sample vial. The sample vial includes a side wall and a bottom wall, and contains a liquid sample. The plunger cap includes a filter plug where the filter plug includes the ion exchange foam described above. The liquid sample is displaced out of the sample vial through the filter plug. A portion of the ions are removed from the liquid sample, at the same time of the displacing, when the liquid sample flows through the filter plug.

In regards to the method of removing ions from a liquid sample, the displaced liquid sample can load a sample loop of an injection valve where the method further includes injecting the liquid sample to a chromatographic separation device. At least one analyte can be separated from matrix components in the liquid sample on the chromatographic separation device. An analyte separated from the matrix components can be detected at a detector. The displacing of the liquid sample through the filter plug can have a flow rate ranging from about 0.5 mL per minute to about 10 mL per minute at a pressure of 50 pounds per square inch or less where the ion exchange foam is in the form of a cylinder with a diameter of about 5 millimeters and a length of about 10 millimeters. The ion exchange foam can have a permeability ranging from about $1 \times 10^{-11}$ $m^2$ to about $1 \times 10^{-16}$ $m^2$.

An autosampler is described that includes a sample vial, a plunger cap, and a filter plug. The sample vial is configured to remove ions from a liquid sample and then transfer the liquid sample to an injection valve. The sample vial includes a side wall, a bottom wall, and an inlet opening. The plunger cap is configured to be pushed into the sample vial along the side wall and towards the bottom wall, and displace the liquid sample. A filter plug is coupled to an outlet of the plunger cap where the filter plug includes an ion exchange foam as described above. The autosampler further includes a plurality of sample vial sockets configured to hold a plurality of sample vials, a fluid delivery assembly that is configured to deploy and retract the plunger cap for one sample vial at a time, and a drive motor configured to increment a position of the plurality of sample vial sockets so that a subsequent sample vial can be aspirated.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 2 illustrates a cross-sectional view of a sample delivery needle, a vial cap, and a sample vial where the vial cap and the sample delivery needle are in an unengaged state.

FIG. 3 illustrates a cross-sectional view of the sample delivery needle engaged with the vial cap where the sample delivery needle is partially deployed to dispense fluid out of the sample vial.

FIG. 4 shows an expanded cross-sectional view of the sample delivery needle engaged with the vial cap that illustrates a position of a filter plug that removes ions.

DETAILED DESCRIPTION OF EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

A foam is a material that contains a plurality of bubbles. More particularly, a foam can be a cross-linked polymeric material that contains a plurality of void spaces that approximate interconnected spheres. In an embodiment, foam materials can be synthesized that contain bound ion exchange material. This binding process may be caused by physical entrapment of the ion exchange material within the void volumes as the foam forms a crosslinked structure. Alternatively, the ion exchange material may be entrapped in the void volume via a combination of chemical binding and physical entrapment. The ion exchange material can be in the form of a resin substrate. As used herein, a resin refers to a polymeric substrate. Ion exchange foams have unique properties that allow a relatively high loading of ion exchange material per unit volume while at the same time providing relatively low backpressure. As such, Applicants found that the ion exchange foams described herein are uniquely suited for simple, fast, and inexpensive sample preparation processing. Liquid samples can be filtered through ion exchange foams to remove matrix ions from a sample in an automated format at low pressures and short cycle times. For convenience, the ion exchange foams can be relatively low cost, disposable, and have sufficient capacity to bind a substantial portion of matrix chemicals for at least one sample aliquot. The following will describe a method to synthesize such ion exchange foams.

Figure 1:
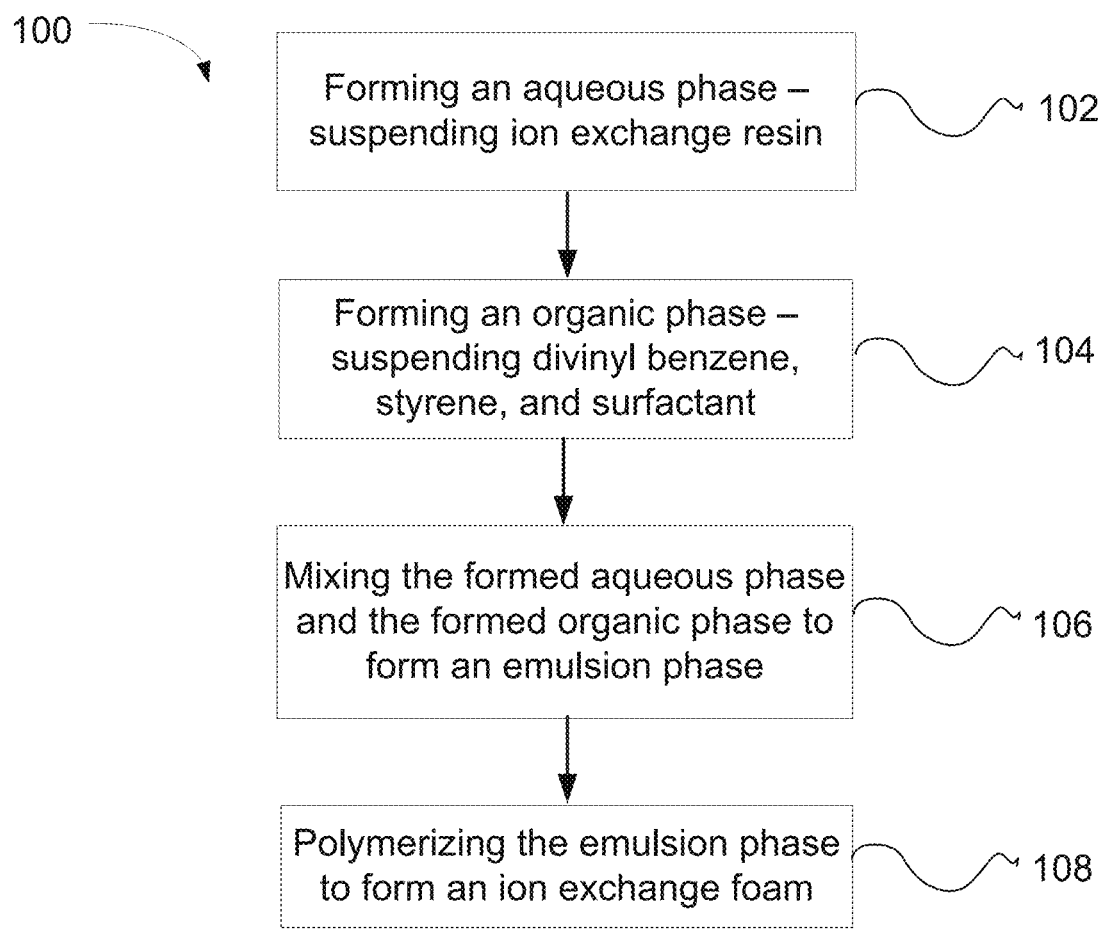
FIG. 1 is a flow chart illustrating a method of making an ion exchange foam.

FIG. 1 is a flow chart illustrating a method 100 of making an ion exchange foam. In a step 102, an aqueous phase is formed by suspending at least one ion exchange resin in an aqueous solvent. Next, an organic phase is formed by mixing at least a divinylbenzene, a styrenic monomer, and a surfactant, as shown in a step 104. The formed aqueous phase and the formed organic phase can be mixed together to form an emulsion, as shown in a step 106. Once the emulsion has been formed, it can be polymerized to form the ion exchange foam, as shown in a step 108.

In regards to the step 102, the ion exchange resin includes a matrix that is insoluble in water and typically in the form of spherical beads. In an embodiment, the beads may have a diameter ranging from about 2 microns to about 100 microns, preferably ranging from about 5 microns to about 25 microns, and more preferably ranging from about 4 microns to about 20 microns. The ion exchange resin may have a pore size ranging from about 10 angstroms to about 150 angstroms. The ion exchange resin can be suspended in an aqueous phase by magnetic stirring and/or sonication. The aqueous phase may be deionized water. The ion exchange resin may be one of the following types that are strong cation exchange, weak cation exchange, strong anion exchange, and weak anion exchange. An example of a strong cation exchange resins is a crosslinked styrene sulfonate. An example of a weak cation exchange resin is an acrylate polymer matrix such as the commercially available Bio-Rex® 35-70 μm, 200-400 mesh (Bio-Rad, Hercules, Calif., USA). An example of a strong anion exchange resin is an alkyl quaternary ammonia group such as the commercially available CarboPac (Thermo Scientific Dionex, Sunnyvale, Calif., USA), TSKgel SAX manufactured by Tosoh Corporation (Tokyo, Japan), BioRad AG 1-X8 Anion Exchange Resin 45-106 μm wet (Bio-Rad, Hercules, Calif., USA), and Bio Rex 5 Anion Exchange Resins 45-75 μm wet. In an embodiment of a cation exchange resin, the resin may be in a salt form of a cation exchange resin when suspending in the aqueous phase in accordance with the step 102. The ion exchange resin can have a weight percent range ranging from about 25% to about 75%. The weight percent can be calculated by dividing the weight of the resin by the total weight of the resin and the water (i.e., [gram of resin/(gram of resin+grams of water)]×100%)). Preferably, a pH should be provided that causes the resin to be predominantly in the salt form. An initiator is added to the aqueous phases such as, for example, persulfate. Under certain circumstances where the initiator is an anion (e.g., persulfate) and the ion exchange resin is an anion exchange resin, it may be more suitable to use a cationic water soluble initiator to reduce the likelihood that the anionic initiator is bound to the ion exchange resin. An example of cationic water soluble initiators is 2,2'-azobis[2-(2-imidazolin-2-yl)propane]dihydrochloride (catalog number VA44 that is commercially available from Wako Chemical Co, Japan).

In regards to the step 104, the organic phase may have a mixture of monomer, cross-linker, and surfactant. Examples of the monomer and cross-linker may be styrenic monomer and divinyl benzene. The styrenic monomer may include an underivatized styrene monomer or a styrene monomer derivatized with a variety of functional groups. Another embodiment of a monomer that may be suitable for use herein includes acrylate monomer and methacrylate monomer. In an embodiment, a molar ratio of styrene to divinyl benzene may range from about 2:1 to about 80:1. The surfactant may be in the form of an oil soluble surfactant or more particularly a non-ionic oil soluble surfactant. An example of a surfactant suitable for synthesizing an ion exchange foam is sorbitan monooleate (e.g., SPAN 80). It should be noted that a surfactant may include a block co-polymer based on polyethylene oxide or polypropylene oxide that have both hydrophilic and hydrophobic domains. The surfactant is used to facilitate the formation of the emulsion. In an embodiment, the organic phase does not have an added solvent.

In regards to the step 106, the formed aqueous phase and the formed organic phase are mixed together to form an emulsion. In an embodiment, the organic phase may be mixed at about 400 rotations per minute using a D-shaped polytetrafluoroethylene (PTFE) stirrer blade. The aqueous phase may then be added to the stirred organic phase in a dropwise manner using a peristaltic pump or a dropping funnel to form the emulsion. The aqueous phase can be pumped into the organic phase at a flow rate that corresponds to a percent volume of the organic phase per minute, which can range from about 0.5% per minute to about 25% per minute. The percent volume of the organic phase per minute can be calculated based on the following: [flow rate of aqueous phase (mL/min)/volume of organic phase (mL)]×100%. The emulsion includes a dispersed aqueous phase and a continuous organic phase.

In regards to the step 108, the formed emulsion is polymerized to form an ion exchange foam. In an embodiment, the emulsion can be heated to a temperature sufficient to initiate an initiator. For example, the heating may be at about 60° C. when using persulfate initiator. The initiator can then form a free radical to initiate a free radical polymerization process. Before heating the emulsion, it can be added to a cylindrical container so that the ion exchange foam can have an approximately cylindrical shape after the polymerization. In an alternative embodiment, a conical container like a pipette tip may be used to form a conical shaped ion exchange foam. In addition to a heat based polymerization process, other polymerization processes may be suitable for use in making the ion exchange foams described herein such as, for example, photopolymerization and irradiating the emulsion with an ionizing radiation source.

Using method 100, an ion exchange foam is formed that includes about 40% to about 60% ion exchange resin by volume (i.e., volume of ion exchange resin/volume of foam× 100%). It should be noted that the ion exchange foam may also be referred to as a high internal phase emulsion polymer or an open cell foam. Method 100 allows the copolymerization step and incorporation of ion exchange material to occur in a one-pot reaction mixture. This is synthetically simpler than forming a foam substrate first that is subsequently grafted with an ion exchange material. The ion exchange foam includes a copolymer of divinylbenzene and styrenic monomer. The copolymer has a void volume where the ion exchange resin is disposed in the void volume and bound to or entrapped in the ion exchange foam. It should be noted that water can act as a porogen in this system. The void volume is based on a plurality of approximately spherical void volumes that have interconnected channels. A diameter of the spherical void volumes may have a range sufficiently large to physically entrap a smaller ion exchange material. The ion exchange foam can have a high capacity with a capacity per unit volume of greater than 10 milliequivalents per cubic centimeter (mEq/cc), and preferably ranging from about 1 mEq/cc to about 10 mEq/cc. The term milliequivalent refers to the moles of charged ions that can be bound to the ion exchange foam divided by a thousand. In an embodiment, the ion exchange foam has a flow rate ranging from about 0.5 mL per minute to about 10 mL per minute, preferably from about 0.5 mL per minute to about 5 mL per minute, and more preferably from about 2 mL per minute to about 5 mL per minute at a pressure of 50 pounds per square inch or less where the ion exchange foam is in the form of a cylinder with a diameter of about 5 millimeters and a length of about 10 millimeters. The ion exchange foam can have a porosity ranging from about 50% to about 90%, where the porosity is based on the equation [(gram of water+gram of resin)/(gram of water+gram of resin+gram of organic phase)]×100%.

The ion exchange foam can also be characterized in terms of permeability. The ion exchange foam can have a range of approximately cylindrical sizes such as an outer diameter ranging from about 0.4 mm to about 20 mm, and a length ranging from about 6 mm to about 20 mm. The backpressure may be about 50 pounds per square inch and the flow rate through the ion exchange foam filter may range from about 1 to about 5 mL/min. An equation for permeability can be calculated based on Equation 1.

$$\Delta p = u\eta L/B \quad \text{(Eq. 1)}$$

The terms $\Delta p$ is a backpressure, u is a linear velocity of the sample flowing through the filter, $\eta$ is a viscosity of the liquid sample, L is a length of the filter, and B is a permeability of the ion exchange foam. Based on Eq. 1 and the aforementioned parameters, the ion exchange foam can have a permeability ranging from about $1\times10^{-11}$ m$^2$ to about $1\times10^{-16}$ m$^2$.

Now that the ion exchange foams have been described, the following will describe a method of using a sample vial cap to filter out and remove matrix chemicals from a sample. An analyst will often have a large number of sample vials containing samples that need to be analyzed. However, before beginning the analysis testing, a sample pre-treatment needs to be performed to remove matrix chemicals that can interfere with the analysis. Adding a matrix binding agent to the sample vial, mixing the sample vial, and filtering the matrix binding agent from the sample is a manual process that is time consuming and laborious. To implement an automated process, the ion exchange foam can be used as a filter that is incorporated into the vial cap. The sample vial and vial cap are configured so that liquid flows through the vial cap and the filter at a relatively low pressure while at the same time efficiently binding a substantial portion of the matrix chemicals. The pressure range for filtering sample may range from about 10 pounds per square inch to about 100 pounds per square inch.

FIG. 2 illustrates a cross-sectional view of a sample delivery needle 33, a vial cap 54, and a sample vial 44 where the vial cap 54 and the sample delivery needle 33 are in an unengaged state. The sample delivery needle 33 is configured to bind to the vial cap 54. The vial cap 54 is configured to provide a seal at a side wall of the vial cap 54. The sample delivery needle 33 and the vial cap 54 together can be configured to have a piston cylinder mechanism with the sample vial 44 to dispense the liquid sample. A similar sample filtering apparatus is described U.S. Pat. No. 4,644,807 and US Pre-Grant Publication No. 20100224012, which are hereby incorporated by reference herein; however, the filter in this reference was used to remove particulates and/or reduce evaporation.

The sample delivery needle 33 can also be referred to a plunger needle and has a hollow cylindrical rod shaped structure. At one end of the sample delivery needle 33, there is a needle tip 68. The other opposing end of sample delivery needle 33 can be used to transfer the liquid sample 46 to the analysis device. The needle tip 68 is configured to mate to a socket portion 70 of the vial cap 54, as illustrated in FIGS. 2 to 4.

The vial cap 54 is configured to cap the open ended portion of the sample vial 44. Further, the vial cap 54 is also configured to be slidingly engaged with and to seal the side wall of the sample vial 44. The vial cap 54 has a generally concave portion that cooperatively mates with a generally convex lowermost portion of the sample vial 44. A filter 42 is mounted in a counterbore portion of the vial cap 54. In an embodiment, filter 42 can be mounted by a friction fit, as illustrated in FIG. 4.

In operation and use, a liquid sample 46 is held in sample vial 44 and vial cap 54 is configured to close the sample vial 44. The liquid sample 46 is discharged from sample vial 44 by a downward stroke of needle 33 and cap 54. The cap does not begin to move until a tip 68 of the needle is fully seated in a socket 70 of the cap (best shown in FIG. 3). When the sample delivery needle 33 begins to deploy, any air trapped in the sample vial 44 above the sample is discharged first. Once the delivery of the liquid sample 46 begins, it continues until the required sample amount has been drawn or the sample vial 44 is empty.

Sample vial 44 and vial cap 54 are configured such that when the plunger needle 33 is deployed the vial cap 54 remains in the lowest displacement position in the sample vial 44. Thus, the needle presses the vial cap 54 into the sample vial 44 but is withdrawn from the sample vial 44 without the vial cap 54. The cap remains in the vial with the sample pressurized below the cap. In one embodiment, the vial includes a bottom portion configured to fit tightly with cap 54. When the needle sampling tip is retracted, the cap is held in the bottom portion of the vial due to the tight fit and the needle separates from the cap. In various embodiments, the vial and cap are configured to reduce "dead space" in the vial. The bottom of the exemplary vial has a shape corresponding to the cap such that substantially all of the fluid is displaced from the vial when the cap contacts the bottom.

As described above, liquid sample 46 is urged into the needle passageway as the needle displaces fluid in the vial with a downward force. The cap is depressed in the vial by means of needle tip 68 which is engageable with an upper portion of the cap and movable between axially extended and retracted positions. The needle tip has a plug which mates with socket 70 to form a fluid-tight seal. The needle tip has an axially extending passageway which communicates with a passageway of the system.

As sample 46 is removed from vial 44, the liquid flows through filter 42 contained in the plunger cap 54. Filter 42 includes an ion exchange foam that removes a portion of the ions from the liquid sample 46 at the same time of the displacing. After removing liquid sample 46 from the sample vial 44, the liquid sample 46 can load a sample loop of an injection valve. Next, liquid sample from the sample loop can be injected into a chromatographic separation device. At least one analyte from the liquid sample can be separated from matrix components in the chromatographic separation device and the analyte can be detected at a detector.

Figure 5:
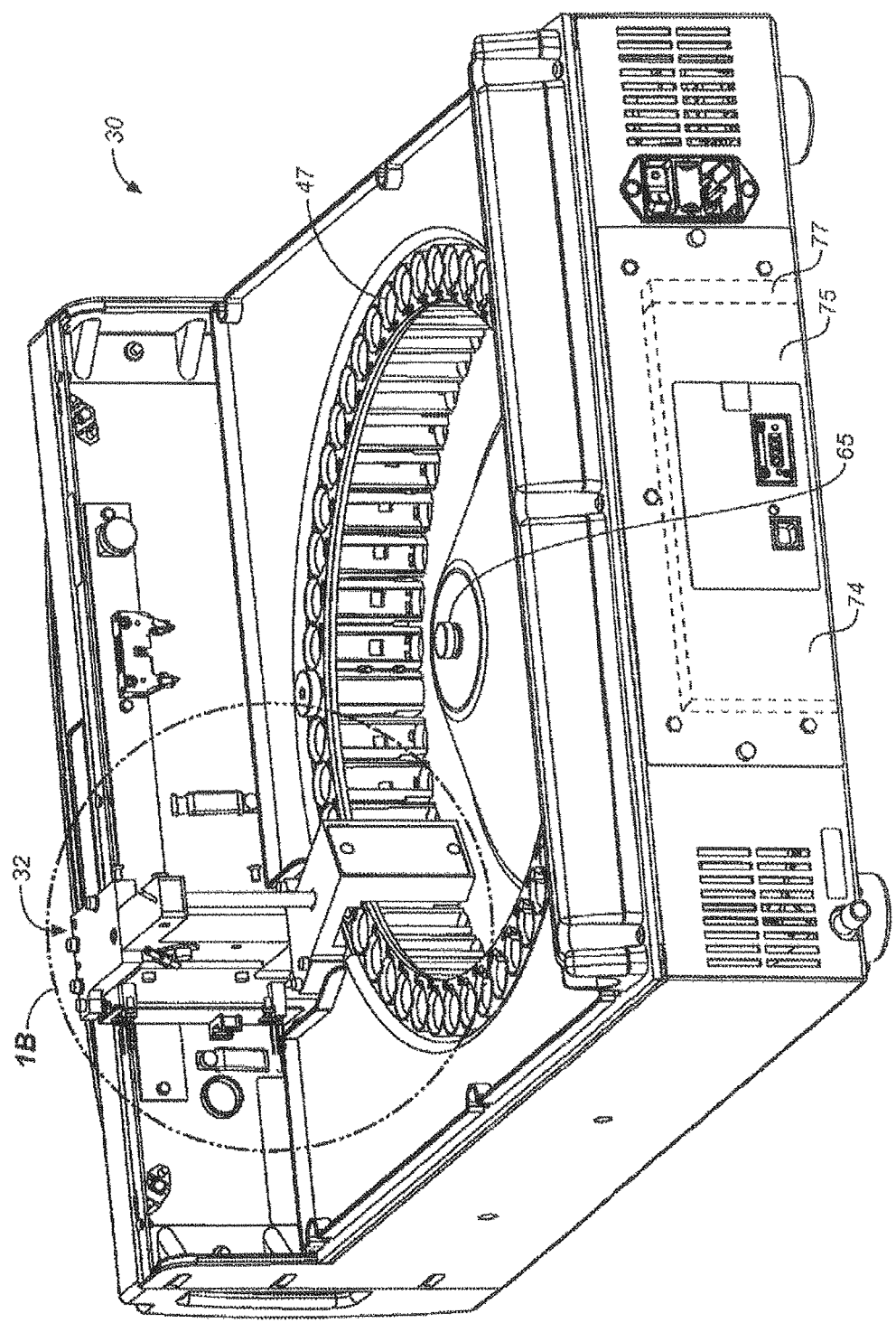
FIG. 5 is a partial perspective view of an autosampler suitable for dispensing liquid samples from a plurality of sample vials and that use the ion exchange foams described herein for removing matrix components.

FIG. 5 is a partial perspective view of an autosampler 30 suitable for dispensing liquid samples from a plurality of sample vials and for use with ion exchange foams described herein. Autosampler 30 is typically used when a large number of samples need to processed in an automated manner. A plurality of sample vials can be loaded on autosampler 30 in an array or carousel format. FIG. 5 illustrates a carousel of sample vial sockets 47 configured to hold a plurality of sample vials. A fluid delivery assembly 32 is configured to deploy and retract the plunger needle for one sample vial at a time as shown in a dotted circle 1B of FIG. 5. The carousel can increment a position so that a subsequent sample vial can be aspirated by rotating around a hub with a drive motor 65. Autosampler 30 also includes a control system 74 that has a microprocessor 75 and a memory 77.

Example 1

A strong cation exchange resin filter cake was prepared. A strong cation exchange resin filter cake was formed by dispersing 28.2 g wet resin (12 g dry resin) in 100 g 1M NaOH solution and sonicated for 5 minutes. The strong cation exchange resin was in the Na$^+$ form and fully sulfonated styrene-divinylbenzene (S-DVB) cation exchange with a particle size diameter of about 9 µm. The solution was then filtered and washed with deionized water in a buchner funnel until the filtrate has a pH value of 7. The resin filter cake was weighed and had a weight of 28.2 g.

Example 2

The strong cation exchange resin filter cake of Example 1 was transferred to a beaker. 0.17 g potassium persulfate as initiator and 84.4 g deionized water were added to the beaker. The aqueous phase was sonicated for 5 minutes and then stirred on a magnetic stirrer plate.

Example 3

0.9 g 80% divinylbenzene, 5.4 g styrene, and 1.1 g SPAN 80 were mixed together in a two-neck round bottom flask. The organic phase was stirred by a D-shape PTFE stirrer blade and the stirrer speed was adjusted to about 400 rpm.

Example 4

The aqueous phase was added to the organic phase drop by drop using a peristaltic pump and with a pumping speed of about 1.25 mL/minute. In this way, a thick creamy stable emulsion was obtained and the emulsion was polymerized in a sealed plastic container at 60° C. for 18 hours. The resulting ion exchange foam was washed with deionized water and acetone and then dried in an oven at 60° C. for overnight. The ion exchange resin trapped emulsion can also be added to and polymerized in a sealed 9×100 mm column body to obtain an ion exchange column. The resulting ion exchange foam was found to have a capacity of about 2 mEq/gram.

Example 5

Figure 6:
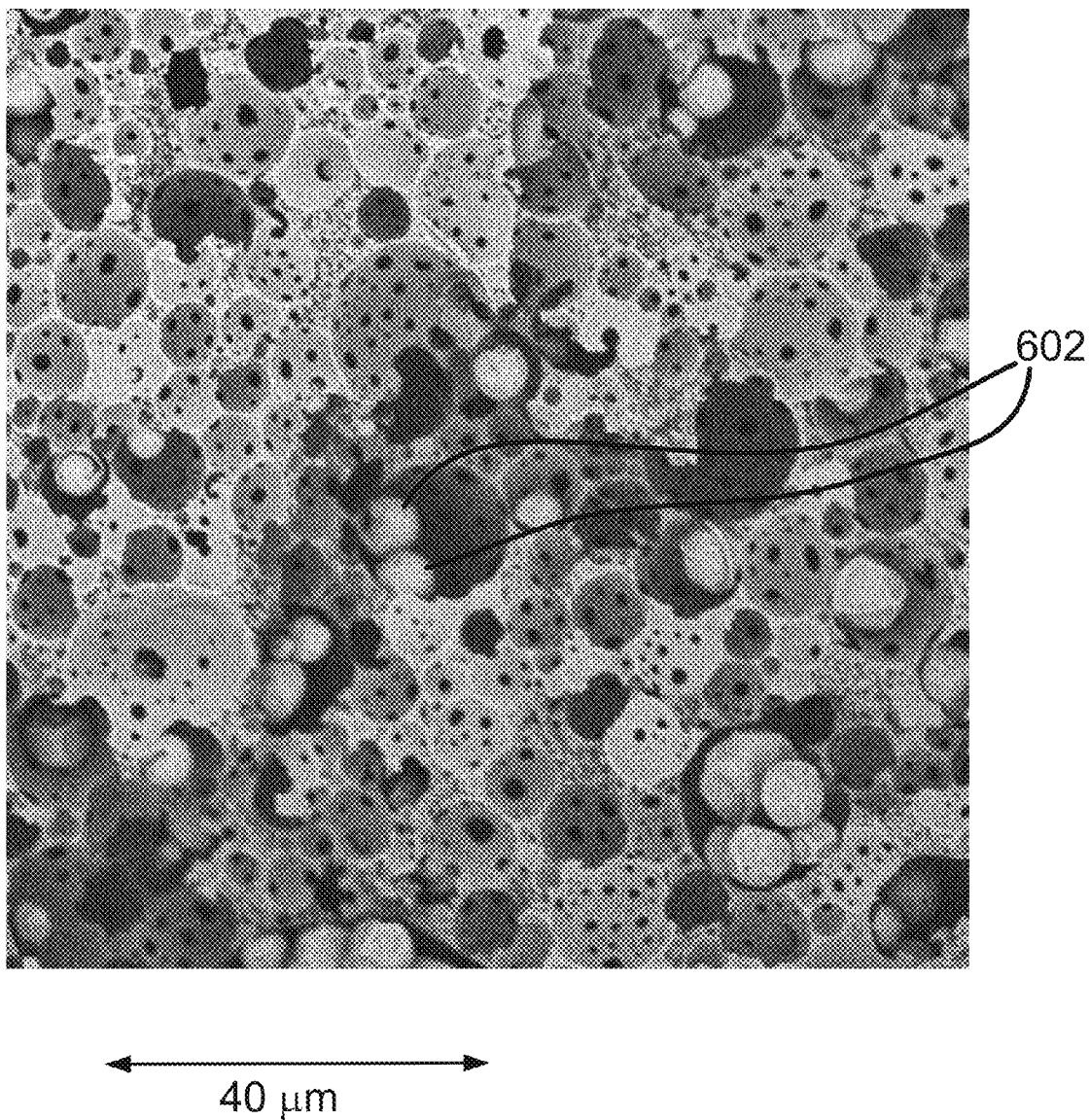
FIG. 6 is a cross-sectional view of a SEM micrograph of an ion exchange foam illustrating a plurality of approximately spherical and interconnected void spaces that include physically entrapped ion exchange particles (2000× magnification).

An ion exchange foam was made similar to the process in Examples 1 to 4 except that the strong cation exchange resin was fully sulfonated S-DVB, 9.5% DVB, 7 micron diameter. This strong cation exchange resin is based on the resin of the commercially available chromatography column from Thermo Scientific Dionex catalog number ICE-AS1 (Sunnyvale, Calif., USA). In regards to the formation of the foam, a 40% by weight divinylbenzene was used with respect to the weight of the styrene and divinylbenzene together. The resulting ion exchange foam was cross-sectioned and analyzed using a scanning electron microscope (SEM). A plurality of void spaces of the foam can be seen in the SEM micrograph of FIG. 6 at a 2000× magnification. In particular, the approximately spherical ion exchange resin particles 602 are illustrated as being physically entrapped in the foam.

Example 6

Figure 7:
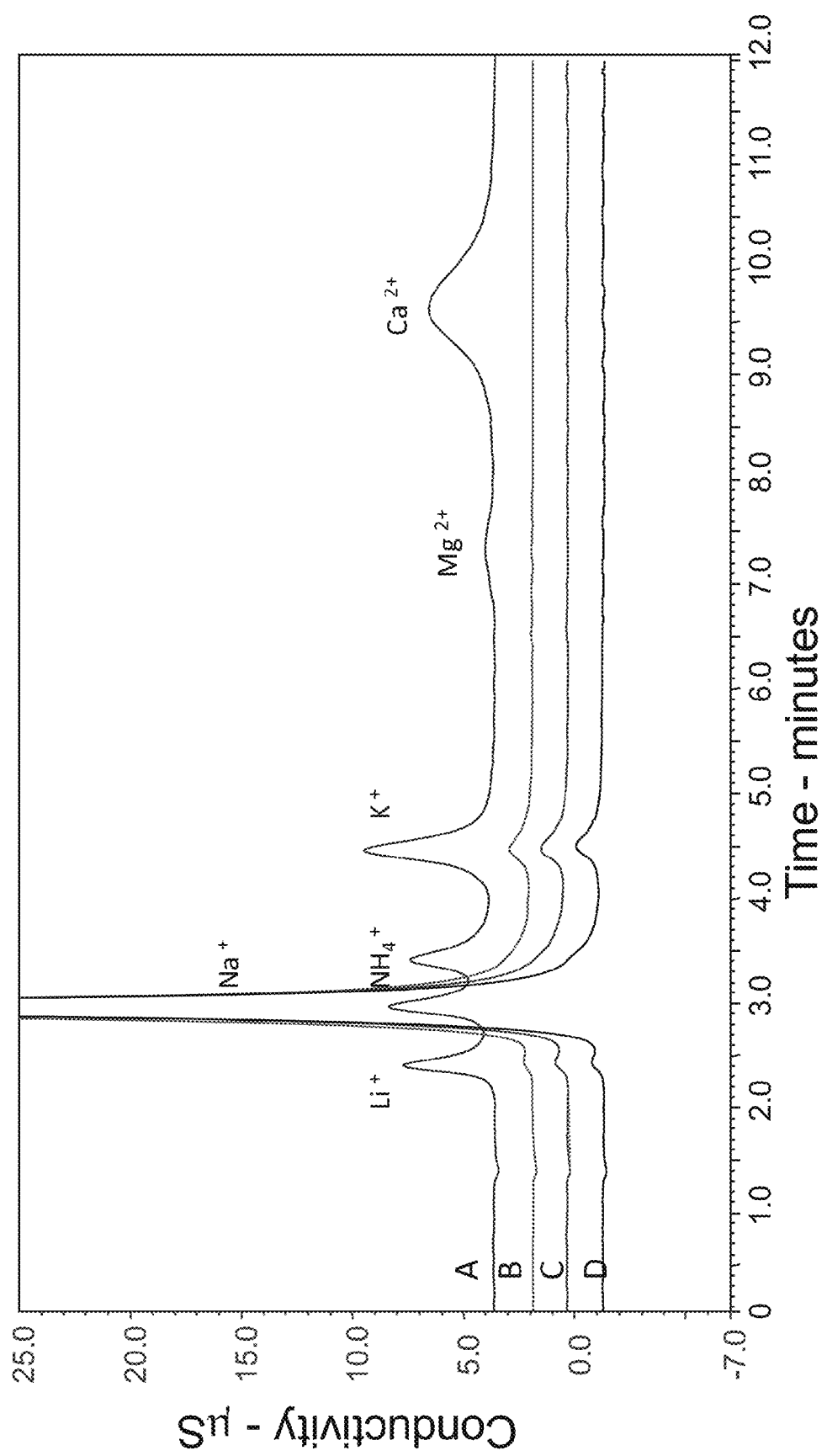
FIG. 7 illustrates an overlay of four chromatograms of an unfiltered sample (A) and three successive aliquots (B-D) of a cation containing sample through an ion exchange foam filter showing that cations were removed.

The ion exchange foam of Example 5 was tested to demonstrate that it bound ions from a flowing sample stream. The ion exchange foam was in sodium form and used as a filter 42 in the vial cap 54 in conjunction with a Thermo Scientific Dionex AS40 autosampler. The filter had a cylindrical shape with a diameter of 5 millimeters and a length of 10 millimeters. The sample vial 44 contained about 6 mL of a sample containing 1 mg/L lithium, 2 mg/L sodium, 2.5 mg/L ammonium, 5 mg/L potassium, 2.5 mg/L magnesium, and 5 mg/L calcium. Three 1.7 mL aliquots of sample were flowed and filtered through one filter 42 in a serial manner. The filtered aliquots were automatically passed to an injection valve loop of an ion chromatograph and subsequently injected for analysis. FIG. 7 illustrates an overlay of four chromatograms of the unfiltered sample (A), first aliquot filtered through filter 42 (B), the second aliquot filtered through filter 42 (C), the third aliquot filtered through filter 42 (D). The analytical system was a Thermo Fisher Dionex ICS5000 chromatography system equipped with a conductivity detector, CS12A analytical column, and CSRS 300 suppressor. The eluent was 20 mM methanesulfonic acid flowing at 1 mL/min. The series of chromatograms (A to D) show that cations ($Li^+$, $NH_4^+$, $H^+$, $Mg^{2+}$, and $Ca^{2+}$) were removed from the sample after flowing through filter 42 and that $Na^+$ was released into the sample from the sodium form of the ion exchange foam. In particular, there was a higher proportion of divalent ions ($Mg^{2+}$ and $Ca^{2+}$) removed from the sample because of the relatively higher charge. Table 1 shows the retention times, peak areas, and peak heights for $Ca^{2+}$ and $Na^+$ with respect to chromatograms A to D.

TABLE 1

| Chromatogram | $Ca^{2+}$ | | | $Na^+$ | | |
| --- | --- | --- | --- | --- | --- | --- |
| | Retention Time - Minutes | Peak Area - mS * min | Peak Height - mS | Retention Time - Minutes | Peak Area - mS * min | Peak Height - mS |
| A | 9.63 | 2.72 | 2.83 | 2.96 | 0.84 | 4.26 |
| B | n.a. | n.a. | n.a. | 2.96 | 12.26 | 63.00 |
| C | n.a. | n.a. | n.a. | 2.97 | 11.96 | 62.28 |
| D | n.a. | n.a. | n.a. | 2.96 | 12.07 | 64.83 |

A theoretical capacity of 0.3 mEq/plug was calculated, which corresponds to 6.6 mL of 1000 ppm calcium. This example demonstrates that the ion exchange foams described herein can withstand moderate pressures without losing structural integrity. These ion exchange foams eliminate the need to use a filtering glass frit for containing unmodified ion exchange resin from the sample making the filtering process more convenient. It should also be noted that structurally rigid foams provide an advantage over packed ion exchange resin particles in that packed ion exchange resin particles can form channels when exposed to turbulent liquid flow. Such channels can dramatically reduce the efficiency of removing ions from the sample liquid because the liquid does not interact with the resin particles. Further, the ion exchange foams tailor the material so that the overall backpressure is reduced to a moderate level while at the same time providing a material that retains a substantial portion of the ion exchange capacity.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of making an ion exchange foam, the method comprising:
   forming an aqueous phase by suspending an ion exchange resin in an aqueous solvent;
   forming an organic phase by mixing at least a divinylbenzene, a monomer, and a surfactant;
   mixing the formed aqueous phase with the formed organic phase to form an emulsion; and
   polymerizing the emulsion to form the ion exchange foam.

2. The method of claim 1, in which the ion exchange foam includes from about 40% to about 60% of ion exchange resin by volume.

3. The method of claim 1, in which the ion exchange foam has an exterior shape that is approximately cylindrical.

4. The method of claim 1, in which the ion exchange foam has an exterior shape that is approximately conical.

5. The method of claim 1, in which the surfactant comprises an oil soluble surfactant.

6. The method of claim 1, in which the surfactant comprises a non-ionic oil soluble surfactant.

7. The method of claim 1, in which the surfactant comprises a sorbitan monooleate.

8. The method of claim 1, in which the surfactant comprises a block co-polymer.

9. The method of claim 1, in which the polymerizing comprises heating the emulsion to a temperature sufficient to initiate an initiator.

10. The method of claim 9, in which the initiator is dissolved in the aqueous phase.

11. The method of claim 9, in which the initiator comprises a persulfate.

12. The method of claim 1, in which the polymerizing comprises illuminating the emulsion with an intensity sufficient to initiate an initiator.

13. The method of claim 1, in which the initiator comprises a cationic water soluble initiator and the ion exchange resin comprises an anion exchange resin.

14. The method of claim 1, in which the polymerizing comprises irradiating the emulsion with an ionizing radiation source at an intensity sufficient to initiate a polymerization.

15. The method of claim 1, in which the ion exchange resin comprises a salt form of a cation exchange resin.

16. The method of claim 1, in which the ion exchange resin comprises a material selected from the group consisting of a styrene sulfonate, a weak cation exchange resin, a strong anion exchange resin, a weak anion exchange resin, and a combination thereof.

17. The method of claim 1, in which the heating is at about 60° C.

18. The method of claim 1, in which the ion exchange material comprises a high internal phase emulsion polymer.

19. The method of claim 1, in which the monomer is selected from the group consisting of a styrenic monomer, acrylate, methacrylate, and a combination thereof.

20. The method of claim 1, in which the monomer is a styrenic monomer.

* * * * *